United States Patent [19]

Motta

[11] 4,105,703

[45] Aug. 8, 1978

[54] CONTINUOUS PROCESS FOR THE PRODUCTION OF CYCLOHEXYL MAGNESIUM HALIDES

[75] Inventor: Raimondo Motta, Pero (Milan), Italy

[73] Assignee: Oxon Italia S.p.A., Milan, Italy

[21] Appl. No.: 819,988

[22] Filed: Jul. 28, 1977

Related U.S. Application Data

[63] Continuation of Ser. No. 692,506, Jun. 3, 1976, abandoned.

[30] Foreign Application Priority Data

Jun. 6, 1975 [IT] Italy .............................. 24100 A/75

[51] Int. Cl.$^2$ .............................................. C07F 3/02
[52] U.S. Cl. .................................. 260/665 G; 23/283
[58] Field of Search ....................... 260/665 G; 23/283

[56] References Cited

U.S. PATENT DOCUMENTS

| | | | |
|---|---|---|---|
| 2,385,200 | 9/1945 | Friedel | 261/DIG. 72 X |
| 2,464,685 | 3/1949 | Hirsch | 260/665 G |
| 2,615,906 | 10/1952 | Stanton | 260/665 G X |
| 2,905,537 | 9/1959 | Copenhaver | 23/283 |
| 4,032,298 | 6/1977 | Blackmar et al. | 260/665 G |

OTHER PUBLICATIONS

Marvel et al., J.A.C.S. 50, 2810-2812 (1928).

*Primary Examiner*—Helen M. S. Sneed
*Attorney, Agent, or Firm*—Young & Thompson

[57] ABSTRACT

Process and apparatus for the production, in a continuous cycle, of cyclohexyl magnesium halides according to which cyclohexyl halide is fed from the bottom, at a constant rate, into a thermostatized column containing magnesium shavings fed from the top of the column itself, and the desired cyclohexyl magnesium halide is recovered in the top part of the column, the temperature of the column being kept at about 58°–60° C and the cyclohexyl halide being fed in a solution of tetrahydrofuran.

5 Claims, 1 Drawing Figure

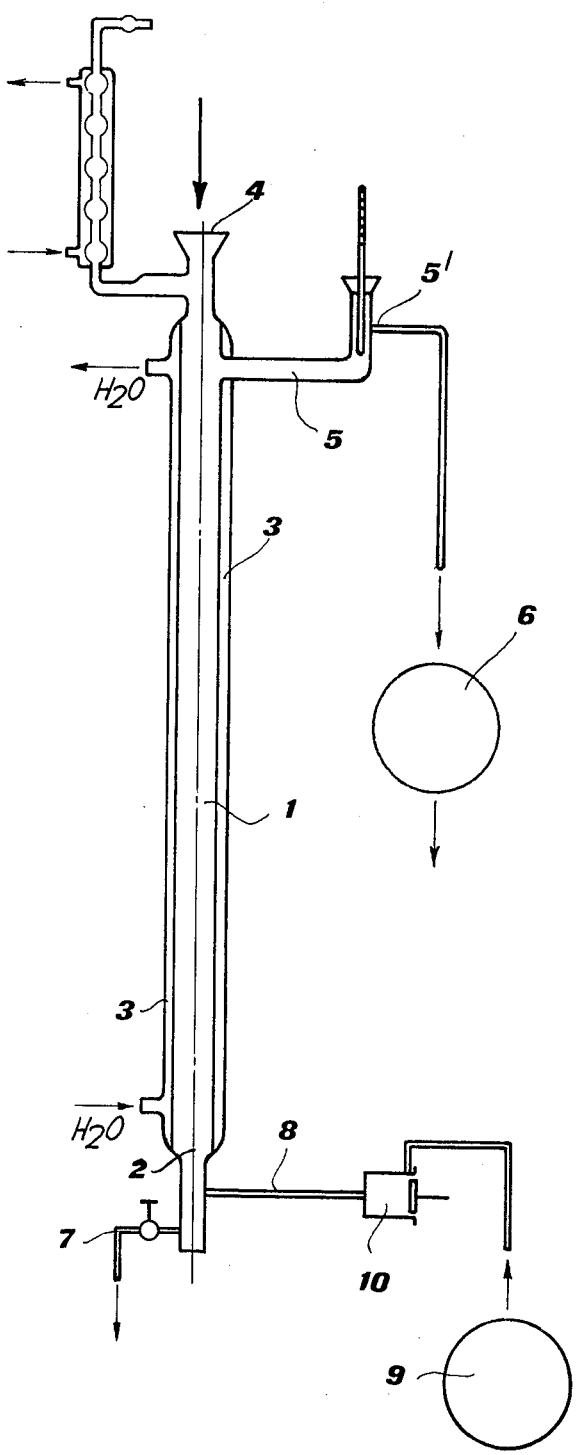

CONTINUOUS PROCESS FOR THE PRODUCTION OF CYCLOHEXYL MAGNESIUM HALIDES

This is a continuation of application Ser. No. 692,506, filed June 3, 1976, now abandoned.

BACKGROUND OF THE INVENTION

The present invention relates to a process for the production, in a continuous cycle, of cyclohexyl magnesium halides.

As known, the cyclohexyl magnesium halides are products which have recently acquired a lot of importance, for example for the production of tricyclohexyl tin derivatives, as the tricyclohexyl tin halides and the tricyclohexyl tin hydroxides, which are very useful as herbicides.

The cyclohexyl magnesium halides are at present produced with a discontinuous process. Such a process has its drawbacks, as there is always — while carrying out the reaction at the basis thereof:

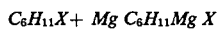
$$C_6H_{11}X + Mg \rightarrow C_6H_{11}MgX$$

wherein $X$ is a halogen (especially $Cl$)—the possibility of explosions, in the event that an excessive amount of halide should be fed when the reaction has not yet started. Moreover, the reaction does not always develop in a complete way, and it is anyhow necessary for it to be carried out in an inert atmosphere.

All such drawbacks are eliminated by the continuous process according to the present invention, which further includes, compared to the known process, all the advantages of continuous productions.

SUMMARY OF THE INVENTION

The process according to the invention is characterized in that cyclohexyl halide is fed from the bottom, at a constant rate, into a thermostatized column containing magnesium shavings fed from the top of the column itself, and the desired cyclohexyl magnesium halide is recovered in the top part of the column. Preferably, the column temperature is kept at about 58°–60° C and the cyclohexyl halide is fed in a solution of tetrahydrofuran, the cyclohexyl magnesium halide being also obtained in tetrahydrofuran solution.

The invention also relates to the apparatus for carrying out said process, which consists of a thermostatized column, having at the bottom a filling of Raschig rings and being provided in the top part with a spillway, having a discharge tube and a tank, and with a top feeding mouth, while the bottom part of said column is connected through a feed pipe to a pump ending into a tank.

BRIEF DESCRIPTION OF THE DRAWING

The invention is no described in further detail with reference to the accompanying drawing, which schematically illustrates the synthesis apparatus used, supposing to carry out the reaction between cyclohexyl chloride and magnesium.

DESCRIPTION OF THE PREFERRED EMBODIMENT

With reference to the drawing, use is made — for the process according to the invention — of a column 1, having a diameter of 5 cm. and a volume of 2000 ml., containing at the bottom 2 a filling of about 3 cm. of Raschig rings, and being thermostated at 58°–60° C through circulation from the bottom upwards of $H_2O$ into a jacket 3. Said column comprises at the top a feeding mouth 4 and in its top part a spillway 5, connected through a discharge 5' to a tank 6, while in the lower part of the column, which also comprises a drain cock 7, there is a feed pipe 8, into which the product contained in a tank 9 is caused to flow through a constant delivery pump 10.

According to the process of the invention, the column 1 is filled from the feeding mouth 4, with shavings (about 420 gr.), up to the height of the discharge 5'. About 200 ml. of 34–35% Grignard reagent solution in tetrahydrofuran are then charged into the column; one waits for the inner temperature to reach 58°–60° C and then one starts to feed through the pipe 8 an anhydrous solution of cyclohexyl chloride in tetrahydrofuran — in the proportions of 650 gr. of tetrahydrofuran and 290 gr. of cyclohexyl chloride — in a quantity of 1 kg. per hour. As one continues to feed said solution from the pipe 8, the reaction product consisting of a 34–35% Grignard reagent solution in tetrahydrofuran, starts to come out from the spillway 5. Said solution is collected into the appropriate tank 6.

The reaction yield, calculated on the cyclohexyl chloride, is of 96–98%. The magnesium wastes away mainly onto the bottom of the column 1 whereby the shavings of this metal slowly drop down along the column itself; this latter is kept constantly filled by frequently adding shavings through the feeding mouth.

With this technique, there appears to be no formation of residues, whereby there is no need for a periodic cleaning of the column.

To interrupt the production, it is anyhow sufficient to stop the feeding from the pipe 8, to cool down the apparatus and to keep the column 1 filled in anhydrous conditions. To start again the production, the inner temperature is brought back to 58°–60° C and the cyclohexyl chloride solution is fed again from the pipe 8.

Compared to the known discontinuous techniques, the continuous process according to the invention, for the preparing of cyclohexyl magnesium halides, has first of all the advantage of being less dangerous, both because of the reduced quantities of products in the cycle, and because of the elimination of the risks connected with the starting of the reaction. In fact, the reaction column can be kept full of Grignard reagent and of Mg, in rest conditions at ambient temperature, even for prolonged periods of time, and then it cam be started again, in conditions of normal efficiency, after having been brought back to the reaction temperature. (On the other hand, this make it indispensable to use a solvent, which will keep the Grignard reagent in solution, at ambient temperature, so as not to have precipitations in the column).

A further advantage of the process according to the invention is that the path followed by the magnesium, according to the type of feeding adopted, allows the same to reach the reaction area in condition of maximum reactivity. It is hence possible to obtain a complete reaction with a single passage of the halide into the column, without having to resort the recycles.

The fact should not be neglected, moreover, that the tests carried out so far have not revealed the need to carry out the reaction in an inert gas atmosphere, as was always required in the known discontinuous processes; this is probably due to the fact that, in the process using the apparatus according to the invention, the reaction takes place in an area which is definitely out of contact with air.

I claim:

1. Continuous process for the production of cyclohexyl magnesium halide (Grignard reagent) characterized in that, cyclohexyl halide in a solution of tetrahydrofuran is fed from the bottom, at a constant rate, into a thermostatized column containing magnesium shavings fed from the top of the column itself, and the desired cyclohexyl magnesium halide is recovered in the top part of the column.

2. Process as in claim 1, wherein the temperature of the column is kept at about 58°–60° C and the cyclohexyl halide is fed in a solution of tetrahydrofuran, the cyclohexyl magnesium halide being also obtained in a tetrahydrofuran solution.

3. Process as in claim 1, wherein, upon starting, a solution of cyclohexyl magnesium halide in tetrahydrofuran is introduced into the column, before starting to feed the cyclohexyl magnesium halide.

4. Apparatus for the continuous production of cyclohexyl magnesium halide (Grignard reagent), comprising a thermostatized column, means for feeding cyclohexyl halide in a solution of tetrahydrofuran into the bottom of the column at a constant rate, means for feeding magnesium shavings into the top of the column, and means for recovering the desired cyclohexyl magnesium halide in the top part of the column.

5. Apparatus as claimed in claim 4, the column having at the bottom a filling of Raschig rings and having at the top part a spillway having a discharge tube and a tank and a top feeding mouth, while the bottom part of the column is connected through a feed pipe to a pump fed by another tank.

* * * * *